United States Patent
Wang et al.

(10) Patent No.: US 10,774,355 B2
(45) Date of Patent: Sep. 15, 2020

(54) GENETICALLY-ENGINEERED MYCOBACTERIUM STRAIN AND A USE THEREOF IN THE PREPARATION OF STEROIDAL COMPOUNDS

(71) Applicant: East China University of Science and Technology, Shanghai (CN)

(72) Inventors: Fengqing Wang, Shanghai (CN); Liqin Xu, Shanghai (CN); Yongjun Liu, Shanghai (CN); Haohao Liu, Shanghai (CN); Liangbin Xiong, Shanghai (CN); Dongzhi Wei, Shanghai (CN)

(73) Assignee: East China University Of Science And Technology, Shanghai (CN)

( * ) Notice: Subject to any disclaimer, the term of this patent is extended or adjusted under 35 U.S.C. 154(b) by 88 days.

(21) Appl. No.: 16/310,741

(22) PCT Filed: Jun. 16, 2016

(86) PCT No.: PCT/CN2016/085972
§ 371 (c)(1),
(2) Date: Dec. 17, 2018

(87) PCT Pub. No.: WO2017/214919
PCT Pub. Date: Dec. 21, 2017

(65) Prior Publication Data
US 2019/0264249 A1    Aug. 29, 2019

(51) Int. Cl.
| | | |
|---|---|---|
| *C12P 33/00* | (2006.01) | |
| *C12P 33/02* | (2006.01) | |
| *C12N 9/02* | (2006.01) | |
| *C12R 1/325* | (2006.01) | |
| *C12R 1/33* | (2006.01) | |
| *C12R 1/34* | (2006.01) | |
| *C12R 1/32* | (2006.01) | |

(52) U.S. Cl.
CPC ............ *C12P 33/00* (2013.01); *C12N 9/0093* (2013.01); *C12P 33/02* (2013.01); *C12R 1/325* (2013.01); *C12R 1/33* (2013.01); *C12R 1/34* (2013.01); *C12R 1/32* (2013.01); *C12Y 117/05001* (2013.01)

(58) Field of Classification Search
None
See application file for complete search history.

(56) References Cited

FOREIGN PATENT DOCUMENTS

CN    101490241 A    7/2009

OTHER PUBLICATIONS

Genbank; "GenBank accession No. CP006936.2"; GenBank database; Aug. 26, 2014.

*Primary Examiner* — Suzanne M Noakes
*Assistant Examiner* — Jae W Lee
(74) *Attorney, Agent, or Firm* — Boyle Fredrickson S.C.

(57) ABSTRACT

The present invention relates to a genetically-engineered *Mycobacterium* strain and a use thereof in the preparation of steroidal compounds. The genetically-engineered *Mycobacterium* strain is a *Mycobacteria* which lacks of acyl-CoA dehydrogenase genes fadE31, fadE32 and fadE33, wherein acyl-CoA dehydrogenase genes fadE31, fadE32 and fadE33 respectively encode proteins as follows: having amino acid sequences according to SEQ ID NOs 4, 6 and 8; derived by substituting, deleting or inserting one or more amino acids in the amino acid sequence defined by preceding protein and having the same function as that of the preceding protein. The present invention constructs a genetically-engineered *Mycobacterium* strain and applies it in preparing steroidal compounds, thereby enriching the types of valuable intermediates, improving the production efficiency and product quality of steroid drugs, reducing energy consumption in the steroid drugs production, simplifying production steps, and reducing production costs.

5 Claims, 6 Drawing Sheets

Specification includes a Sequence Listing.

HIL standard substance      Product

GENETICALLY-ENGINEERED MYCOBACTERIUM STRAIN AND A USE THEREOF IN THE PREPARATION OF STEROIDAL COMPOUNDS

CROSS-REFERENCE(S) TO RELATED APPLICATION(S)

This application is a Section 371 U.S. National Phase Entry of International Patent Application No. PCT/CN2016/085972, having a priority international filing date of Jun. 16, 2016, now the entire contents of which are hereby expressly incorporated by reference into the present application. This application also claims priority to Chinese Patent Application No. CN20168057388, the entirety of which is incorporated herein by reference.

FIELD OF THE INVENTION

The present invention relates to the technical field of genetic engineering, and more particularly to the technical field of acyl-CoA dehydrogenase, in particular to four acyl-CoA dehydrogenase genes and genetically-engineered strains thereof and a use thereof in the preparation of steroidal compounds.

BACKGROUND OF THE INVENTION

Steroidal compounds, also known as steroids, are a class of compounds with perhydrocyclopentanophenanthrene as mother nucleus and having similar structures. As illustrated below, the basic structure consists of three six-membered rings and a five-membered ring, respectively known as A, B, C, and D rings. Taking the four-membered ring sterane mother nucleus as the matrix, the type, configuration and substitution site of substituents can determine the characters and the functions of different steroidal compounds, and form a series of compounds with unique physiological functions. Among them, the steroid having a hydroxyl substituent at C-3, two methyl groups at C-18 and C-19 and a long hydrocarbon side group mostly in β-configuration at C-17 can be collectively referred to as sterol (3-β sterol), for example, cholesterol, ergosterol and the like. In humans and animals, steroids are the main endogenous hormones, which are secreted by sexual organs and the adrenal cortex, and is closely related to reproduction, brain and bone development, steady state maintenance and regulation of biological effects and so on. As an exogenous hormone, steroid hormone drugs also are a class of indispensable clinical drugs, which play an important role in regulating the body and have extremely important medical value. For example, an adrenocortical hormone has anti-inflammatory, antiallergic, antiallergy, anti-shock response and other effects. In addition, the steroid also has many non-hormonal functions, such as antiviral, neoplastic ailments therapy and the like. Therefore, steroidal drugs are widely used in clinical practice, and are the second largest class of drugs with the production only after antibiotics.

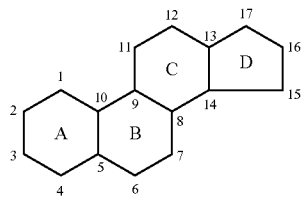

The high demand for steroidal drugs has promoted a vigorous development of another important industry—the extraction and preparation of steroidal drug intermediates (steroidal drugs precursor). The preparation of the steroidal drug intermediate is mainly based on the microbial metabolism of sterol. Mycobacterium has gained widespread attention for its excellent biological metabolism among many microorganisms which could degrade the sterol. Therefore, it's particularly important to analyze the sterol metabolism mechanism of Mycobacterium species. The progress of sterol degradation by Mycobacterium is complicated, and can be divided into two major parts, namely, the degradation of the mother nucleus and the degradation of the side chain. The degradation of the mother nucleus can be divided into the degradation of A and B rings and the degradation of C and D rings, wherein, the research on the degradation mechanism of A and B rings is more adequate and detailed than that of C and D rings.

The acyl-CoA dehydrogenase, as shown in FIG. 1, was speculated by the researchers to be one of the key enzymes involved in degradation of the C and D rings of sterol nucleus, which can participate in the dehydrogenation reaction during the degradation of the C and D rings. The C and D rings are opened and eventually degraded to form $CO_2$ and $H_2O$. Therefore, deletion of the gene encoding acyl-CoA dehydrogenase in Mycobacteria is likely to prevent the degradation process of the C and D rings, thereby producing valuable steroidal drugs intermediates. Until now, valuable intermediates produced from sterol metabolized by Mycobacteria can be mainly divided into C19-steroids (AD, ADD, 9-OHAD, testosterone, boldenone) and C22-steroids (20-carboxy-pregn-4-en-3-one, 4-BNC; 20-hydroxymethyl-pregn-4-en-3-one, 4-BNA; and corresponding 9α-hydroxylation and/or C1 (2) dehydrogenation compounds of each substance and so on). Since the degradation mechanisms of C and D rings have not been thoroughly analyzed, the Mycobacteria strains used to produce the steroidal drug intermediates that retain only the C and D rings are very rare. A valuable compound that can be used for commercialization in the degradation of C and D rings is a lactonization product (sitolactone, HIL) of 5-OHHIP which retains the complete C and D, and it can be used in production of mifepristone, estrogen, and the other steroid drugs. In the steroid medical industry, for the production of sitolactone, the Nocardia bacteria are used to ferment sterol to form 5-OHHIP, followed by pH adjustment, so that 5-OHHIP is lactonized to form commercial sitolactone. The sitolactone production strain is relatively inefficient, and the steps are cumbersome, and thus it has certain defects.

Therefore, it's necessary to study the acyl-CoA dehydrogenase gene to overcome the problems that the degradation mechanism of C and D rings that are unknown, and the sitolactone production strain is lacking, and thus to achieve the transformation and development of high-efficiency production strain, enrich the types of valuable intermediates, improve the production efficiency and product quality of steroids drugs, reduce energy consumption in the steroid drugs production, simplify production steps, and reduce production costs.

SUMMARY OF THE INVENTION

The main object of the present invention is to provide a genetically-engineered Mycobacterium strain and a use thereof in the preparation of steroidal compounds, thereby achieving the development of efficient production strains, enriching the types of valuable intermediates, improving the production efficiency and product quality of steroid drugs, reducing energy consumption in the production of steroid drugs, simplifying production steps, and reducing production costs.

In order to solve the above technical problems, the present invention adopts the following technical solutions:

According to a first aspect of present invention, a genetically-engineered *Mycobacterium* strain is provided, the genetically-engineered *Mycobacterium* strain is a *Mycobacteria* which lacks of acyl-CoA dehydrogenase genes fadE31, fadE32 and fadE33; wherein the acyl-CoA dehydrogenase gene fadE31 encodes a protein (i) or (ii) as follows: (i) having an amino acid sequence according to SEQ ID NO 4; (ii) derived by substituting, deleting or inserting one or more amino acids in the amino acid sequence defined by (i) and having the same function as that of the protein of (i); the acyl-CoA dehydrogenase gene fadE32 encodes a protein (iii) or (iv) as follows: (iii) having an amino acid sequence according to SEQ ID NO 6; (iv) derived by substituting, deleting or inserting one or more amino acids in the amino acid sequence defined by (iii) and having the same function as that of the protein of (iii); the acyl-CoA dehydrogenase gene fadE33 encodes a protein (v) or (vi) as follows: (v) having an amino acid sequence according to SEQ ID NO 8; (vi) derived by substituting, deleting or inserting one or more amino acids in the amino acid sequence defined by (v) and having the same function as that of the protein of (v).

The present invention realizes the selective deletion of acyl-CoA dehydrogenase gene through genetic manipulation, and constructs a genetically-engineered *Mycobacterium* strain without acyl-CoA dehydrogenase gene activity, which is achieved by targeted, unlabeled genetic engineering manipulation of the acyl-CoA dehydrogenase genes.

Preferably, the proteins encoded by the acyl-CoA dehydrogenase genes fadE31, fadE32 and fadE33 have at least 75% identity to the amino acid sequences according to SEQ ID NOs 4, 6 and 8, respectively. More preferably, they have a consistency of 80% or more, and still more preferably have a consistency of 90% or more.

The nucleotide sequence of acyl-CoA dehydrogenase gene fadE31 is the following sequence (1) or (2): (1) a nucleotide sequence shown at positions 889-2037 of the sequence according to SEQ ID NO 3; (2) a nucleotide sequence that has at least 70% identity to the nucleotide sequence shown in the sequence (I); The acyl-CoA dehydrogenase gene fadE32 has the following sequence (3) or (4): (3) having a nucleotide sequence shown at positions 889-1845 of the sequence according to SEQ ID NO 5; (4) having a nucleotide sequence that has at least 70% identity to the nucleotide sequence shown in the sequence (3); The acyl-CoA dehydrogenase gene fadE33 has the following sequence (5) or (6): (5) having a nucleotide sequence shown at positions 889-1821 of the sequence according to SEQ ID NO 7; (6) having a nucleotide sequence that has at least 70% identity to the nucleotide sequence shown in the sequence (5).

The sequences shown in SEQ ID NOs 3, 5, and 7 except for the nucleotide sequences of the acyl-CoA dehydrogenases fadE31, fadE32, and fadE33 contain a regulatory element and neighboring gene fragment of the enzyme. The three genes of acyl-CoA dehydrogenase genes fadE31, fadE32 and fadE33 are adjacent in gene cluster and overlapping with each other by several bp bases.

Preferably, the acyl-CoA dehydrogenase genes fadE31, fadE32 and fadE33 have nucleotide sequences that have at least 60% identity to the sequences according to SEQ ID NOs 3, 5 and 7, respectively. More preferably, they have a consistency of 70% or more, and still more preferably have a consistency of 80% or more.

The acyl-CoA dehydrogenase gene is derived from *Actinomycetes*, more preferably, *Mycobacterium* microorganism and *Rhodococcus* microorganism.

More preferably, the acyl-CoA dehydrogenase gene is derived from the *Mycobacterium* microorganism.

More preferably, the *Mycobacterium* microorganism is a fast growing type of *Mycobacterium*.

Further, the fast growing type of *Mycobacterium* is *Mycobacterium* sp. NRRL B-3683, *Mycobacterium* sp. NRRL B-3805, *Mycobacterium smegmatism*, *Mycobacobacterium fortuitum*, *Mycobacterium gilvum*, *Mycobacterium neoaurum*, *Mycobacterium Phlei*, *Mycobacterium avium* or *Mycobacterium vanbaalenii*.

Further, the fast growing type of *Mycobacterium* is *Mycobacterium* neoaurum.

Most preferably, the acyl-CoA dehydrogenase gene is derived from the fast growing type of *Mycobacterium neoaurum NwIB*-00.

According to a second aspect of the present invention, a use of a genetically-engineered *Mycobacterium* strain which lacks of acyl-CoA dehydrogenase genes fadE31, fadE32 and fadE33 in the preparation of steroidal compounds is further provided.

The steroidal compound is sitolactone.

The use compromises of: inoculating the genetically-engineered *Mycobacterium* strain as described above into a culture medium, and then adding sterol as a substrate, which is converted and degraded to form sitolactone.

The so-called sterol is an important natural active substance widely distributed in living organisms and is classified into three categories: animal sterol, phytosterol, and fungi sterol according to their source materials. Animal sterol is mainly cholesterol, and there are many sources of phytosterol, for example, deodorizer distillates in vegetable oil processing, and tarot oil in pulp and paper industry, etc. Phytosterol is usually a mixture, usually containing sitosterol, stigmasterol, campesterol, brassicasterol and etc. The ergosterol belongs to the fungi sterol.

In addition, the present invention also relates to an acyl-CoA dehydrogenase gene fadE30 and a *Mycobacteria* lacking of acyl-CoA dehydrogenase gen fadE30. Wherein, the acyl-CoA dehydrogenase gen fadE30 encodes the following protein: having an amino acid sequence according to SEQ ID NO 2; or derived by substituting, deleting or inserting one or more amino acids in the amino acid sequence defined by the preceding amino acid sequence and having the same function as that of the preceding protein. The acyl-CoA dehydrogenase gene fadE30 has the following sequence: having a nucleotide sequence shown at positions 748-1896 of the sequence according to SEQ ID NO 1 or having a nucleotide sequence that has at least 70% identity to the nucleotide sequence shown in the preceding sequence.

The functions of the four genes of acyl-CoA dehydrogenases fadE30, fadE31, fadE32, and fadE33 are all annotated as acyl-CoA dehydrogenases. The four genes are in the same gene cluster where the gene fadE30 exists alone, and fadE31, fadE32 and fadE33 are adjacent and overlapping with each other by several bp bases.

However, according to the study of the present invention, the *Mycobacteria* lacking the acyl-CoA dehydrogenase fadE30 gene is not satisfactory in the sitolactone preparation. Thus, the main achievement of the invention is: firstly, the present application, for the first time, clarify that the genes involved in the sitolactone (HIL) preparation are acyl-CoA dehydrogenases fadE31, fadE32, and fadE33, but not acyl-CoA dehydrogenase fadE30, which was never mentioned in previous reports; secondly, the present application, also for the first time, deletes the acyl-CoA dehydrogenase fadE31, fadE32 and fadE33 genes in *Mycobacteria*, and provides a genetically-engineered strain lacking acyl-CoA dehydrogenase fadE31, fadE32 and fadE33 genes simultaneously, thereby realizing the preparation of steroidal compounds, especially sitolactone.

In conclusion, the present application provides a genetically-engineered *Mycobacterium* strain and its use in the preparation of steroidal compounds. By deleting the acyl-CoA dehydrogenase genes fadE31, fadE32, and fadE33 in *Mycobacteria*, a genetically-engineered *Mycobacterium* strain is obtained and is used to prepare the sitolactone. The product purity is high and the production procedure is simplified, which can greatly improve the production efficiency of steroid drugs, enrich the types of valuable intermediates, reduce energy consumption in the steroid drugs production, simplify production steps, and reduce production costs. Besides, the reaction conditions are mild and environmentally friendly, which is suitable for promotion and application and has high economic and social benefits.

Figure 1:
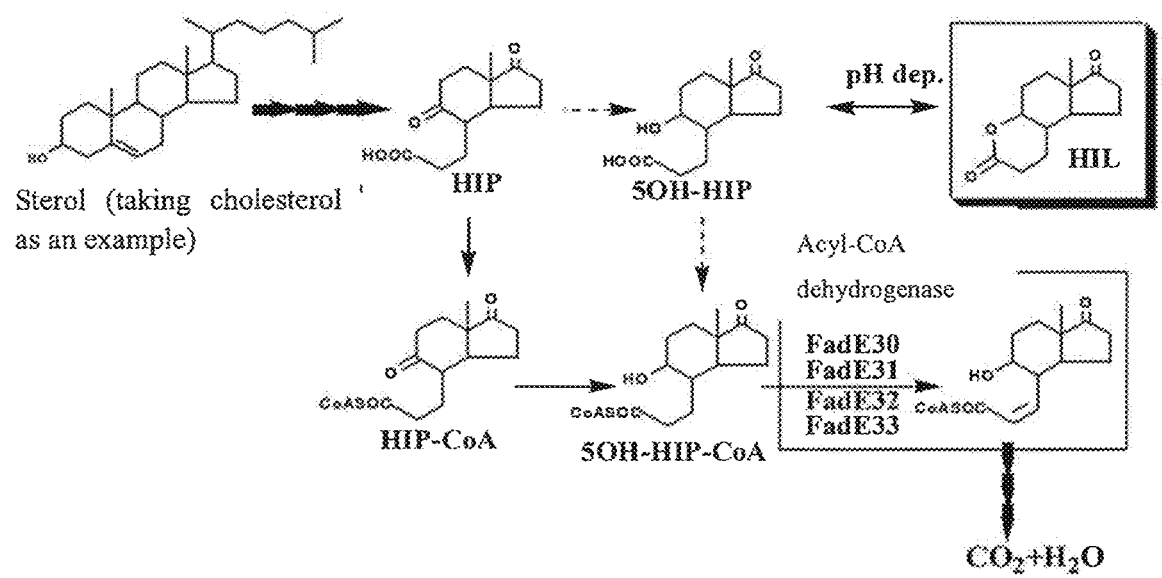
FIG. 1 is a schematic diagram showing the degradation process of the sterol mother nucleus C and D rings, and the reaction formula and key enzymes in the microbial degradation of sterol to prepare sitolactone (HIL)

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected, attached, or terms similar thereto are often used. They are not limited to direct connection but include connection through other elements where such connection is recognized as being equivalent by those skilled in the art.

DESCRIPTION OF THE PREFERRED EMBODIMENTS

In order to better understand the present invention, the invention is further described in connection with following specific embodiments. It should be understood that the following embodiments are intended to illustrate the invention and are not intended to limit the scope of the invention.

The experimental methods, if no specific condition is indicated, in the following examples, are generally carried out according to conventional conditions, as described in Molecular Cloning: Laboratory Manual (New York: Cold Spring Harbor Laboratory Press, 1989).

The gene manipulation technique employed in the present invention is mainly an unlabeled enzyme function inactivation technique. The unlabeled enzyme function inactivation technology mainly comprises: non-resistant markers in-frame deletion of hydroxyacyl-coenzyme A dehydrogenase gene.

The *Escherichia coli* DH5a and pMD19-T vectors used in the embodiments of the present invention are purchased from Novagen Corporation and the primers are synthesized by Dalian Takara Corporation.

The substrate used to prepare the steroidal compounds referred to in the present invention is sterol, only for example, "sterol" is a class of 3-alcohol-5-ene-steroidal compounds.

The *Mycobacteria* referred to in the present invention is a non-pathogenic fast growing type of *Mycobacteria*. In order to better understand the present invention, a standard strain NwIB-00 (Accession No. as follows: ATCC 25795) of *Mycobacterium neoaurum* is used as a specific embodiment for further illustration. It should be understood that the following embodiments are intended to illustrate the invention and are not intended to limit the scope of the invention.

Embodiment 1

The Acquisition of Upstream and Downstream Sequences Adjacent to Acyl-CoA Dehydrogenase Gene from *Mycobacterium* NwIB-00 and Construction of Knockout Plasmid The present embodiment takes the construction of acyl-CoA dehydrogenase gene knockout plasmid as an example. By analyzing the whole genome information of *Mycobacterium* NwIB-00, the acyl-CoA dehydrogenase gene and its upstream and downstream sequences were positioned, and PCR amplification primers were designed. The upstream and downstream sequences of the acyl-CoA dehydrogenase gene were obtained from *Mycobacterium* NwIB-00, and ligated into plasmid p2NIL, and then the selection marker in the pGOAL19 plasmid was also ligated into the p2NIL, so as to construct the acyl-CoA dehydrogenase gene knockout plasmid. The specific process is as follows:

1.1 The Acquisition of Upstream and Downstream Sequences of acyl-CoA Dehydrogenase Gene and Design of Knockout Primer.

The whole genome sequencing of *Mycobacterium* NwIB-00 was carried out, according to its sequencing information in combination with the reported gene cluster information of similar strains, the genomic annotation information was searched and the genes annotated with acyl-CoA dehydrogenase function were preliminarily positioned. Finally, the complete reading frame sequences of four genes acyl-CoA dehydrogenase gene fadE30, acyl-CoA dehydrogenase gene fadE31, acyl-CoA dehydrogenase gene fadE32 and acyl-CoA dehydrogenase gene fadE33 in *Mycobacterium* NwIB-00 were determined through pairwise sequence alignment to the corresponding reported genes by software Cluster1 W1.8 and NCBI blast. The upstream and downstream sequences adjacent to acyl-CoA dehydrogenase were obtained by tracking in the whole genome sequencing. Based on the upstream and downstream sequences, the upstream and downstream primers for acyl-CoA dehydrogenase gene knockout were designed using the software Oligo 6.0 and Primer 5.0 as follows:

Firstly, gene fadE30 were positioned, the upstream and downstream sequences of the gene were found afterwards, taking nearly 1 KB gene fragment of the upstream sequences and taking nearly 1 KB gene fragment of downstream sequences, the upstream and downstream primers of the acyl-CoA dehydrogenase gene fadE30 knockout were designed as follows: Q-fadE30-uF (according to SEQ ID NO:9), Q-fadE30-uR (according to SEQ ID NO:10), Q-fadE30-dF (according to SEQ ID NO:11), Q-fadE30-dR (according to SEQ ID NO:12).

Since fadE31, fadE32 and fadE33 are three adjacent sequences which are overlapping with each other by several bp bases, the three genes in the whole genome were positioned firstly during primer design to find the upstream and downstream sequences of the three genes. Taking nearly 1 KB gene fragment of the upstream sequences and taking nearly 1 KB gene fragment of downstream sequences, the upstream and downstream primers for the acyl-CoA dehydrogenase gene fadE31, acyl-CoA dehydrogenase gene fadE32 and acyl-CoA dehydrogenase gene fadE33 successively knockout were designed as follows: Q-fadE3123-Uf (according to SEQ ID NO:13), Q-fadE3123-uR (according to SEQ ID NO:14), Q-fadE3123-dF (according to SEQ ID NO:15), and Q-fadE3123-dR (according to SEQ ID NO:16).

1.2 Construction of acyl-CoA Dehydrogenase Gene fadE30 Knockout Plasmid (QC-fadE30) and Three Genes of acyl-CoA Dehydrogenase Gene fadE31, fadE32 and fadE33 Successively Knockout Plasmid.

The *M. neoaurum* NwIB-00 genome DNA was used as template to carry out PCR amplification using the above primers, the upstream and downstream fragments with acyl-CoA dehydrogenase gene fadE30 knockout, and the upstream and downstream fragments with acyl-CoA dehydrogenase gene fadE31, fadE32 and fadE33 successively knockout were sequentially obtained. The PCR reaction system is as follows: template DNA 0.5 ul, 2× primestar GC Buffer 25 ul, 2.5 mM dNTP 4 ul, primestar DNA polymerase 0.5 ul, each primer (20 umol/L) 0.5 ul and add water to a total volume 50 ul. The PCR reaction conditions are as follows: 98° C. for 2 minutes, 30 cycles at 98° C. for 10 seconds, 65° C. for 8 seconds, 72° C. for 1 minute and 30 seconds, when finished, 72° C. for 10 minutes for extension.

Figure 2:
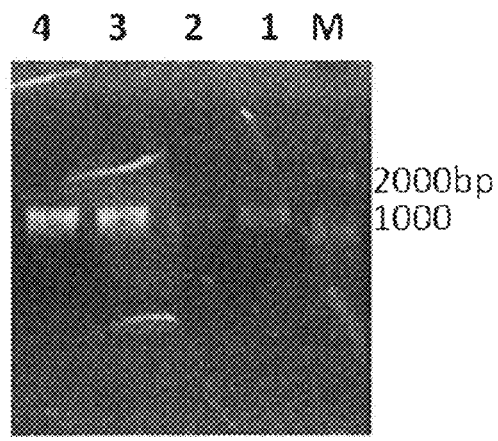
FIG. 2 shows upstream and downstream sequences of acyl-CoA dehydrogenase genes obtained by amplification from the *Mycobacterium* NwIB-00, wherein M is the DNA standard marker; Lane 1 is the upstream sequence of fadE30 gene; Lane 2 is the downstream sequence of fadE31 gene; Lane 3 is the upstream sequence obtained by PCR amplification for construction of fadE31, fadE32 and fadE33 genes knockout plasmids; Lane 4 is the downstream sequence obtained by PCR amplification for construction of fadE31, fadE32 and fadE33 genes knockout plasmids.

The PCR product was tested and the result is shown in FIG. 2 which shows only one SYBR GREEN I staining band. After the gel was recovered, the upstream and downstream genes of the target gene were cloned into the pMD19-T vector for sequencing. The sequencing results were compared with the original sequence and the gene similarity was up to 100%, which indicates that the correct upstream and downstream fragments were obtained.

The upstream fragments of acyl-CoA dehydrogenase gene fadE30-deficient were digested with HindIII and NotI, and the downstream fragments of acyl-CoA dehydrogenase gene fadE30-deficient were digested with NcoI and KpnI respectively. The upstream fragments of acyl-CoA dehydrogenase gene (fadE31, fadE32, and fadE33)-deficient were digested with HindIII and BamHI, and the downstream fragments of acyl-CoA dehydrogenase gene (fadE31, fadE32, and fadE33)-deficient were digested with BamHI and KpnI respectively. The upstream and downstream digested products were ligated to the corresponding digested *Mycobacterium* gene knockout plasmid p2NIL. The above mentioned plasmid and pGOAL19 plasmid were digested with PacI and the selection marker in pGOAL19 plasmid was non-directionally ligated to p2NIL. After screened by double-antibody of kanamycin and hygromycin B and screened by x-gal blue-white spots, the acyl-CoA dehydrogenase gene knockout plasmids QC-fadE30 and QC-fadE3123 are respectively obtained.

Embodiment 2

Construction of *Mycobacterium* NwIB-00 acyl-CoA Dehydrogenase Gene fadE30-Deficient Engineering Strain (NwIB-XE30) and Construction of *Mycobacterium* NwIB-00 acyl-CoA Dehydrogenase Genes (fadE31, fadE32 and fadE33)-Deficient Engineering Strain (NwIB-XE3123).

In the present embodiment, the main technical means and method of homologous recombination and double exchange knockout used in *Mycobacteria* are described by taking the knockout of the acyl-CoA dehydrogenase gene fadE30 as an example, and the knockout of the acyl-CoA genes fadE31, fadE32 and fadE33 is completed by the same method. There are a variety of methods for *Mycobacterium* gene knockout, and the method of gene knockout is not limited here. A gene knockout method developed by Professor Tanya Parish is used as an example here to illustrate the target gene knockout (Bhavna G Gordhan and Tanya Parish, Gene replacement using pretreated DNA, *Mycobacterium* tuberculosis protocols, 2001, pp 77-92).

*Mycobacterium* acyl-CoA dehydrogenase genes knockout plasmids were constructed, and then were electro-transformed into *Mycobacterium*. Screening was carried out with Kanamycin and hygromycin B and then re-screened with sucrose plate was carried out to obtain gene knockout recombinants. The recombinants were validated by PCR.

The present invention is directed to the acyl-CoA dehydrogenase genes knockout from *Mycobacterium* NwIB-00 to obtain two *Mycobacteria* mutant strains named NwIB-XE30, NwIB-XE3123, respectively.

Among them, the NwIB-XE30 strain is obtained by the knockout of the single gene of acyl-CoA dehydrogenase gene fadE30 from the NwIB-00 strain; and the NwIB-XE3123 strain is obtained by the knockout of acyl-CoA dehydrogenase gene fadE31, acyl-CoA dehydrogenase gene fadE32, and acyl-COA dehydrogenase gene fadE33 (there is no order for knockout) from the NwIB-00 strain.

2.1. Transformation of the Knockout Plasmid into *Mycobacterium* Competent Cells

*Mycobacteria* competent preparation: the first grade seed was incubated to OD 0.5-1.5, 5%-10% was transferred into the second grade seed; after 14-24 h, 2% glycine was added and the culture was continuously incubated for about 24 h. The cells were collected by centrifugation and washed with 10% glycerol four times to suspend and then centrifuged. Finally, 1 ml of glycerol were added to suspend cells and stored separately.

Electrotransformation: 10 μL of the above mentioned plasmid treated by alkaline were added to 100 μL of the competent cells for 15 minutes and the electroshock conditions were as follows: 2.5 kv/cm, 25 μF, 20 ms.

2.2 Screening and Validation of Recombinants

The electrotransformation product was added to medium for renewing culture about 3-24 h, and then applied to the solid medium (ingredients: hyg 50 μg/mL, Kn 20 μg/mL, X-gal 50 μg/mL) at 30° C. for 3-7 days until colonies grow on the plate. Blue colonies were picked out and transferred to liquid medium. PCR validation was carried out to validate the recombinant of single-crossover (SCO) has been produced correctly. The verified recombinant of single-crossover (SCO) bacterial were applied to a 2% sucrose plate and cultured at 30° C. for 3-7 days until blue colonies and white colonies appeared simultaneously. The white colonies are picked out and verified by PCR.

Confirmation of recombinants: including PCR validation of the recombinants of single-crossover and the recombinants of double-crossover, and the principle of validation is described in the above cited literature. The acyl-CoA dehydrogenase gene knockout validation primers were Q-fadE30-uF and Q-fadE30-dR.

Figure 3:
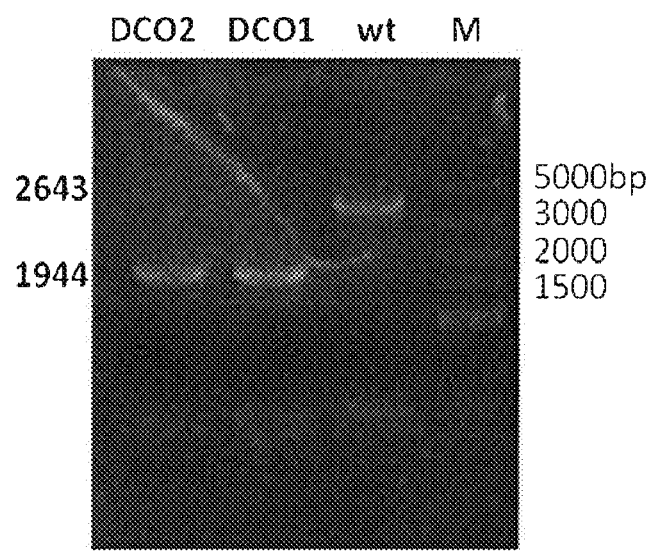
FIG. 3 shows acyl-CoA dehydrogenase gene fadE30-deficient strain is obtained through two-step screening of *Mycobacterium* transformants by the application of existing screening techniques, wherein M is the DNA standard marker; DCO1 is the amplification result of screened recombinant of double-crossover $1^{\#}$; DCO2 is the amplification result of screened recombinant of double-crossover $2^{\#}$; and wt is the PCR amplification result of unknocked strain with the same primers.

The results of the validation are as shown in FIG. 3. As to the strain that has not deleted the acyl-COA dehydrogenase gene fadE30 successfully, only a band of 2643 bp appeared theoretically; and as to the acyl-CoA dehydrogenase gene of the recombinants of double-crossover (DCO), only a band of about 1944 bp (as shown in DCO1 and DCO2) appeared theoretically which is equal to the sum length of upstream and downstream fragments. It indicates that the acyl-CoA dehydrogenase gene fadE30 has been successfully knocked out and the function of the original enzyme has been destroyed.

Experimenter completed the knockout of the acyl-CoA dehydrogenase genes fadE31, fadE32 and fadE33 successfully from the NwIB-00 strain as the method above mentioned and the validation primers are Q-fadE3123-uF and Q-fadE3123-dR.

Figure 4:
FIG. 4 shows acyl-CoA dehydrogenase genes fadE31, fadE32 and fadE33-deficient strain is obtained through two-step screening of *Mycobacterium* transformants by the application of existing screening techniques, wherein. M is the DNA standard marker; DCO1 is the amplification result of screened recombinant of double-crossover 1#; DCO2 is the amplification result of screened recombinant of double-crossover 2#; SCO is the amplification result of the recombinant of single-crossover having both the full-length sequence and the deleted sequence; wt is the PCR amplification result of unknocked strain with the same primers.

The results of the validation are shown in FIG. 4. As to the strain that has not deleted the acyl-COA dehydrogenase gene successfully, only a band of 4805 bp (as shown in wt) appeared theoretically; and as to the acyl-CoA dehydrogenase gene of the recombinants of single-crossover (SCO), two bands of about 4805 bp and 2105 bp (as shown in SCO) appeared theoretically, and as to the acyl-COA dehydrogenase gene of the recombinants of double-crossover (DCO), only a hand of about 2105 bp (as shown in DCO1 and DCO2) appeared theoretically indicating that the acyl-COA dehydrogenase genes fadE31, fadE32 and fadE33 have been successfully knocked out and the function of the original enzyme has been destroyed.

Embodiment 3

Transformation of Sterol by *Mycobacterium* NwIB-00, NwIB-XE30 and NwIB-XE3123 and the Method of Results Analysis.

The sterol substrate was solubilized with 1% to 10% of a surfactant, a polymer or an organic solvent (such as Tween 80, ethanol, silicone oil, soybean oil, etc.). Secondary or tertiary culture was used as seed, 5% to 10% of the seed was inoculated to the final transformation medium, and the sterol substrate can be added at any time. The conditions for steroid transformation were as follows: incubation temperature of 25-37° C., high dissolved oxygen value, pH being able to be controlled between 5.0 and 8.0, and the end time of the conversion reaction being determined by thin layer chromatography (TLC) or gas chromatography (GC) analysis. After the reaction, the steroial transformant can be extracted three times with the same volume of an organic solvent such as ethyl acetate or chloroform. The obtained solution was combined and vacuum dried to carry out analysis and product preparation.

Shake-flask cultivation was adopted to cultivate *Mycobacterium* NwIB-00 to convert phytosterol, 5%-10% of Tween80 or silicone oil was used as a cosolvent of phytosterol, in a 250 mL shake flask with 30 mL volume of sample loading, wherein 5%-10% of the seed was inoculated to a second grade culture containing 0.4-2 g/L of phytosterol and cultured at 26-35° C., 200-300 rpm, pH5.0-8.0. After 3-7 days, ethyl acetate was added to shake and extract, and the organic phase was analyzed by TLC and GC to detect the transformation of sterol.

The operating conditions of thin layer chromatography (TLC) were as follows: petroleum ether:ethyl acetate (6:4 to 7:3) was used as the developing agent; the thin plate was 5×10 cm prefabricated plate produced by Yantai Silicone Factory; The color is visualized by iodine vapor method, namely the iodine crystal and developed TLC plates were placed in a closed vessel, and the developed plates was baked in an oven at 75° C. for 3 minutes-10 minutes until the spots were observed.

The operating conditions of GC were as follows: the inlet temperature was 290° C.; the heating procedure was: 104° C. for 2 minutes, and the temperature was raised to 290° C. at a rate of 15° C./minute, for 15 minutes; the flow rate was 1 ml/minutes, the detection temperature was 300° C. and the column was DB-5.

Figure 5:
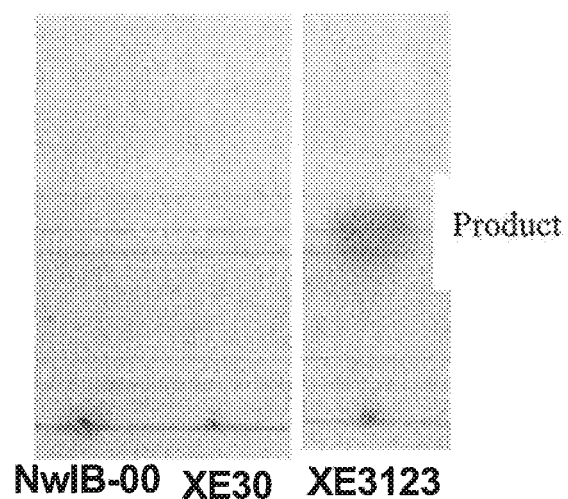
FIG. 5 is a thin layer chromatogram (TLC) map showing the transformation result of phytosterol by *Mycobacterium* NwIB-00, NwIB-XE30 and NwIB-XE3123.
Figure 6A:
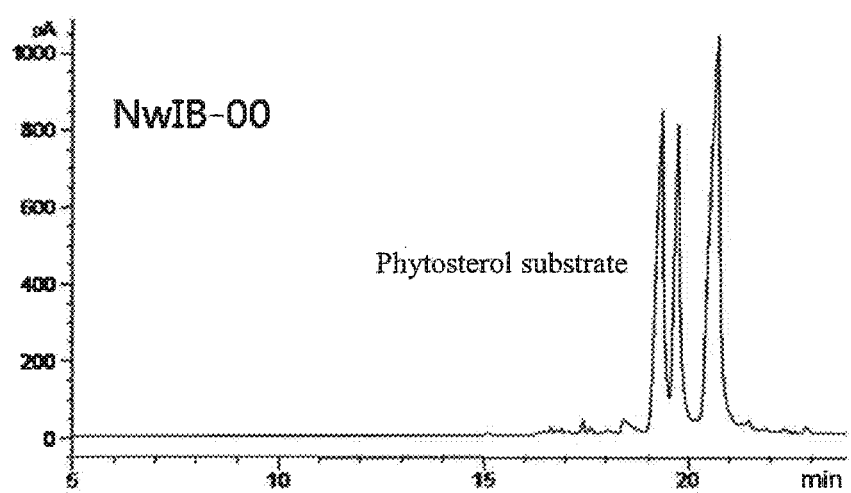
FIG. 6A and FIG. 6B are gas chromatography (GC) maps showing the transformation result of phytosterol by *Mycobacterium* NwIB-00, NwIB-XE30.
Figure 6B:
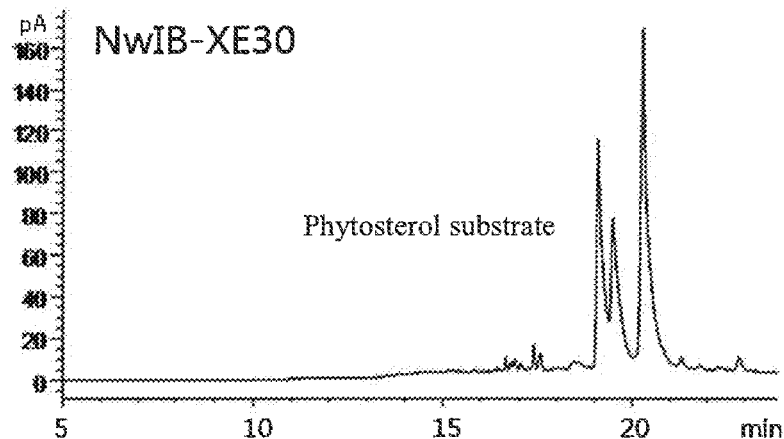

The transformation results of phytosterols by *Mycobacterium* NwIB-00, NwIB-XE30 and NwIB-XE3123 are as shown in FIG. 5 and FIG. 6. Phytosterol can be completely decomposed and metabolized by *Mycobacterium* NwIB-00 without the accumulation of any products. Phytosterol also can be completely decomposed and metabolized by *Mycobacterium* NwIB-30 without the accumulation of any products. Therefore, it indicated that acyl-CoA dehydrogenase gene fadE 30 can't play a key dehydrogenase role in the process of degradation of sterol C and D rings by *Mycobacteria*, while *Mycobacterium* NwIB-XE3123 transforms phytosterol into an unknown product.

Embodiment 4

Identification of Transformation Product of Phytosterol by *Mycobacterium* NwIB-XE3123.

Figure 7:
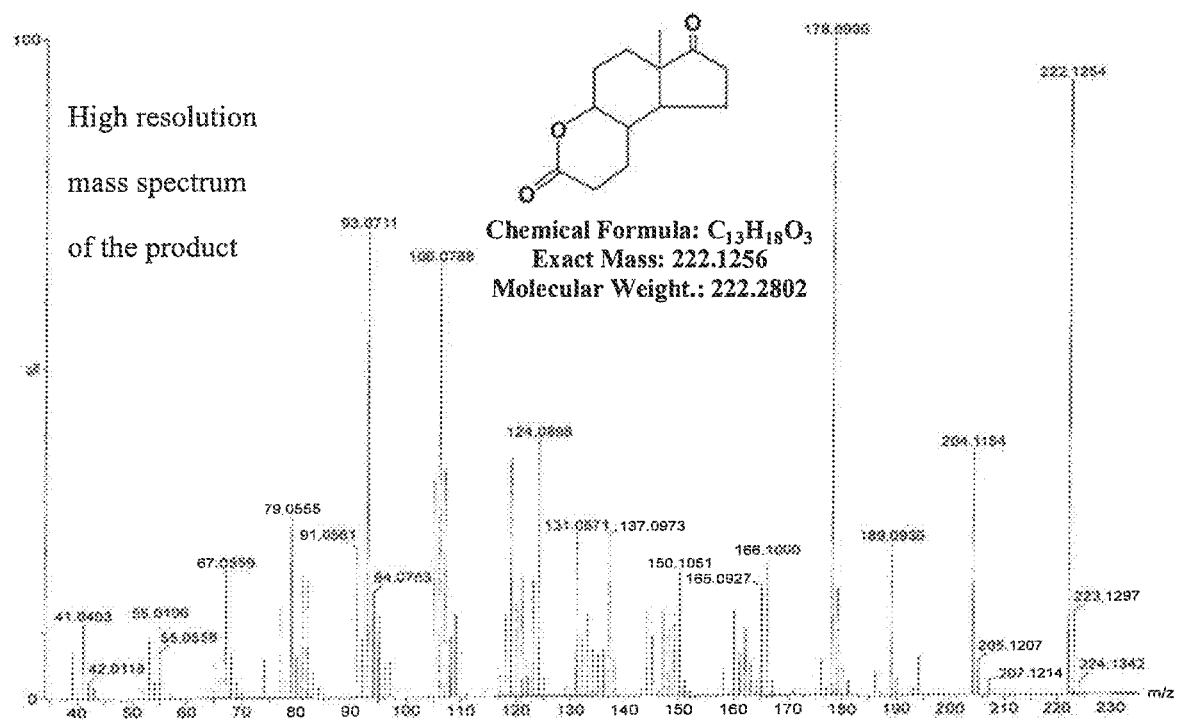
FIG. 7 shows a high resolution mass spectrum and inferred chemical formula and structural formula of the product obtained by transformation of phytosterol by *Mycobacterium* NwIB-XE3123 engineered strain.
Figure 8A:
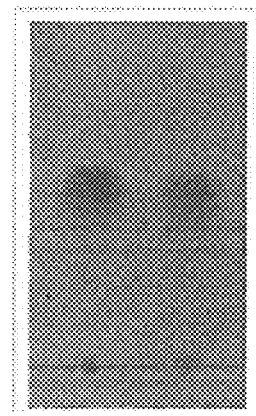
FIGS. 8A, 8B respectively are comparison of TLC, GC maps of transformation product of phytosterol by *Mycobacterium* NwIB-XE3123 engineered strain and sitolactone (HIL) standard substance.
Figure 8B:
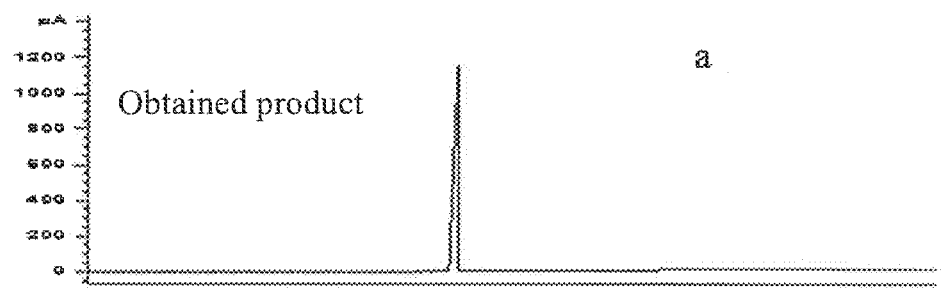
Figure 8B:
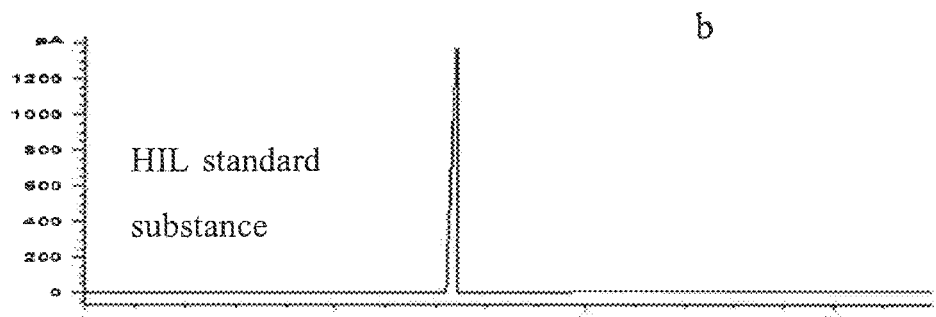
Figure 8C:
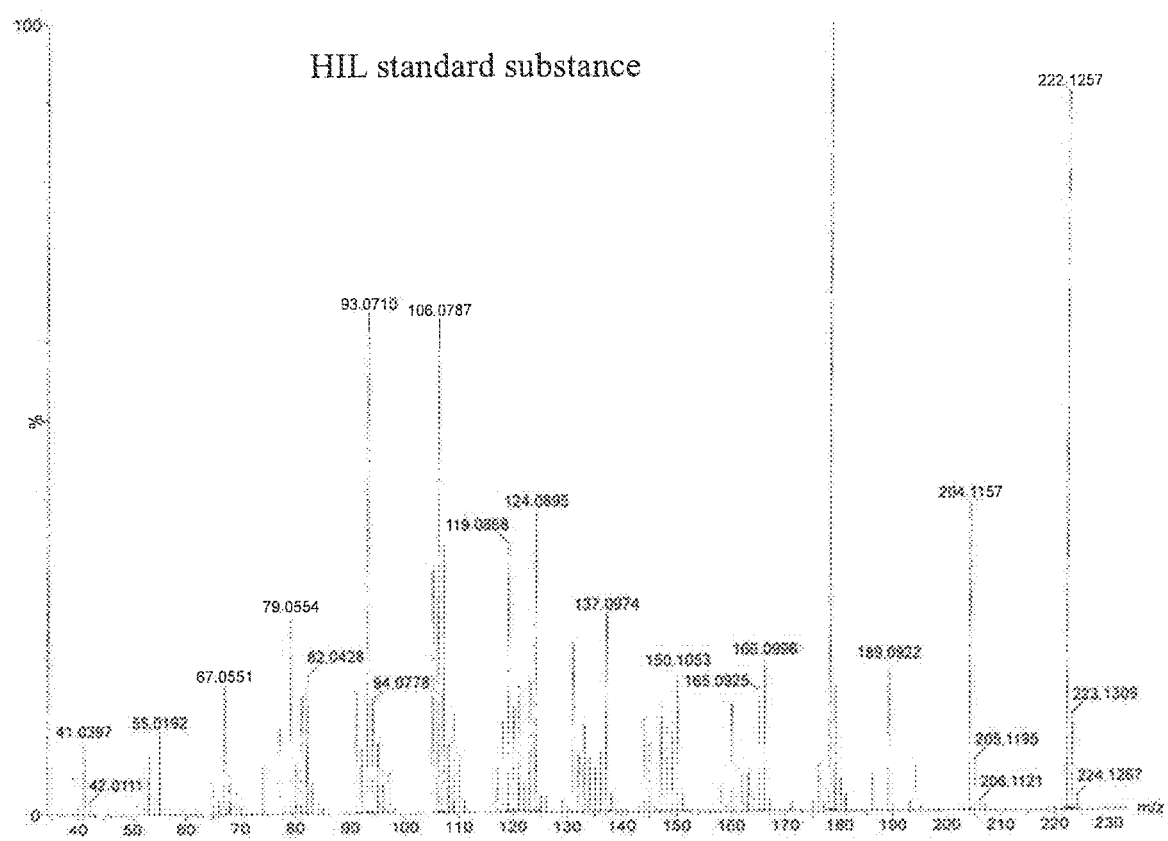
FIG. 8C is high resolution mass spectrum of sitolactone (HIL) standard substance.

The unknown product obtained in embodiment 3 was subjected to product preparation to obtain a dried product powder. As shown in FIG. 7, the high resolution mass spectrometry determined that the product had a molecular of 222.1254 and a chemical formula of $C_{13}H_{18}O_3$. Combined with the general process of sterol C and D rings degradation by *Mycobacteria* (as shown in FIG. 1), it is speculated that this compound is approximately sitolactone (HIL). The sitolactone (HIL) standard substance was purchased, and the standard substance and the product were subjected to TLC dot plate alignment, and simultaneously subjected to GC and high resolution mass spectrometry with the specific methods referred to in embodiment 3. As shown in FIGS. 8A, 8B and 8C, under the same conditions, the obtained product was in the same position as the HIL on the TLC plate, and its peak time on the GC was consistent with the HIL, and the high-resolution mass spectrometry results of the product showed was consistent with the high-resolution mass spectrometry fragments of HIL, and the molecular weight was consistent. Finally, the product was determined as sitolactone.

Embodiment 5

Application of Genetically-Engineered Strain NwIB-XE3123 in Sterol Degradation for Producing Sitolactone.

By analyzing the results of embodiment 3 and 4, it was confirmed that acyl-CoA dehydrogenase genes fadE31, fadE32 and fadE33 play a key role in the degradation of sterol C and D rings; and the genetically-engineered strain NwIB-XE3123 is an ideal strain for sitolactone production.

Figure 9:
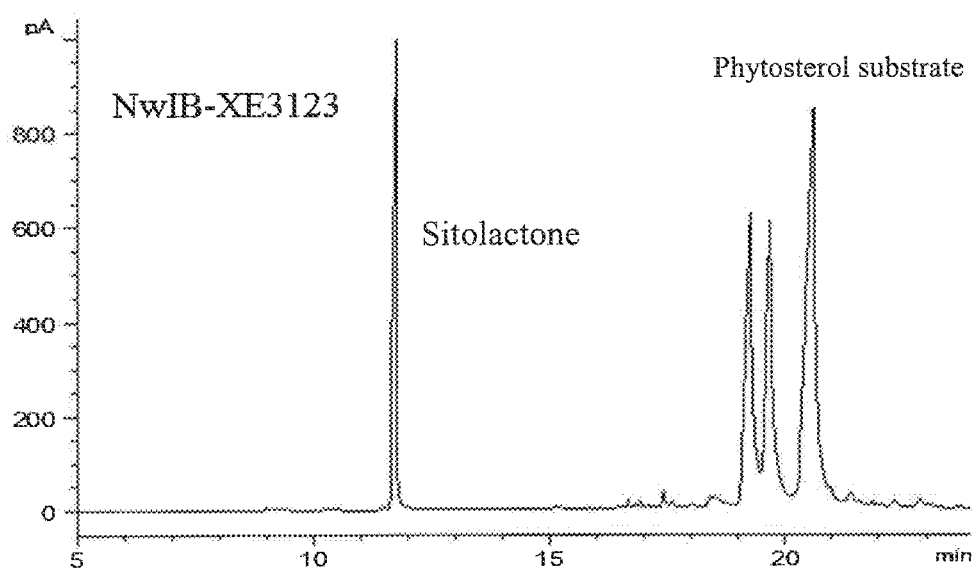
FIG. 9 is a gas chromatography (GC) map showing the results of transformation of phytosterol by *Mycobacterium* NwIB-XE3123 engineered strain.

The culture conditions of the genetically-engineered strain and the transformation conditions of the steroid can be referred to embodiment 3. In the shake flask (30 ml liquid/250 ml shake flask), with phytosterol as the substrate, the feed time is 2 g/L, and the conversion time was 5-10 days, the results of transformation of phytosterols by engineering strains are as shown in FIG. 5 and FIG. 9.

The genetically-engineered strain NwIB-XE3123 transforms and degrades sterol to produce sitolactone. As the TLC and GC results show, excluding the unconsumed phytosterol substrate, the purity of the product sitolactone is high, close to 100%, and the formation of impurities basically can't be detected, which greatly reduces the cost of product purification and separation in the industry.

In summary, the genetically-engineered *Mycobacterium* strain constructed by using acyl-CoA dehydrogenase gene of the present application can efficiently produce high-purity sitolactone, which can be industrially applied to production of mifepristone, estrogen, and other steroid drugs and greatly reduce the cost of purification and separation in the industry. At the same time, the genetically-engineered strain can be used to transform sterol into sitolactone in one step, which simplifies the industrial production steps, improves the production efficiency of steroidal drugs, helps to reduce energy consumption and material consumption in the production process of steroids, and reduces production costs.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept.

Additionally, any of the components described herein could come combined with one another. Furthermore, all the disclosed features of each disclosed embodiment can be combined with, or substituted for, the disclosed features of every other disclosed embodiment except where such features are mutually exclusive.

The aforementioned preferable embodiments are exemplary rather than limiting in nature, and many variations of the present invention are possible in light of the above teachings. It is, therefore, to be understood that all easy, equivalent variations and modifications made according to the claims and description of present invention fall into the scope of the invention as defined by the claims. The contents that have not been described in detail are the routine technical solutions.

It is intended that the appended claims cover all such additions, modifications and rearrangements. Expedient embodiments of the present invention are differentiated by the appended claims.

What is claimed is:

1. A genetically-engineered *Mycobacterium* strain, characterized in that the genetically-engineered *Mycobacterium* strain is a *Mycobacteria* which lacks of acyl-CoA dehydrogenase genes fadE31, fadE32 and fadE33;
   wherein the acyl-CoA dehydrogenase gene fadE31 encodes a protein (i) or (ii) as follows:
   (i) having the amino acid sequence according to SEQ ID NO 4;
   (ii) derived by substituting, deleting or inserting one or more amino acids in the amino acid sequence defined by (i) and having the same function as that of the protein of (i);
   wherein the acyl-CoA dehydrogenase gene fadE32 encodes a protein (iii) or (iv) as follows:
   (iii) having the amino acid sequence according to SEQ ID NO 6;
   (iv) derived by substituting, deleting or inserting one or more amino acids in the amino acid sequence defined by (iii) and having the same function as that of the protein of (iii); and
   wherein the acyl-CoA dehydrogenase gene fadE33 encodes a protein (v) or (vi) as follows:
   (v) having the amino acid sequence according to SEQ ID NO 8;
   (vi) derived by substituting, deleting or inserting one or more amino acids in the amino acid sequence defined by (v) and having the same function as that of the protein of (v),
   wherein said proteins (ii), (iv) and (vi) have at least 75% sequence identity to SEQ ID NOs 4, 6, and 8, respectively.

2. The genetically-engineered *Mycobacterium* strain according to claim 1, characterized in that the acyl-CoA dehydrogenase gene fadE31 has the following sequence (1) or (2):

(1) having a nucleotide sequence shown at positions 889-2037 of the sequence according to SEQ ID NO 3;
   (2) having a nucleotide sequence that has at least 70% identity to the nucleotide sequence of (1);
   wherein the acyl-CoA dehydrogenase gene fadE32 has the following sequence (3) or (4):
   (3) having a nucleotide sequence shown at positions 889-1845 of the sequence according to SEQ ID NO 5;
   (4) having a nucleotide sequence that has at least 70% identity to the nucleotide sequence of (3);
   wherein the acyl-CoA dehydrogenase gene fadE33 has the following sequence (5) or (6):
   (5) having a nucleotide sequence shown at positions 886-1821 of the sequence according to SEQ ID NO 7; and
   (6) having a nucleotide sequence that has at least 70% identity to the nucleotide sequence of (5).

3. The genetically-engineered *Mycobacterium* strain according to claim 1, characterized in that the *Mycobacterium* species is a fast growing type of *Mycobacterium*, and the fast growing type of *Mycobacterium* is selected from a group consisting of: *Mycobacterium* sp. NRRL B-3683, *Mycobacterium* sp. NRRLB-3805, *Mycobacterium smegmatism, Mycobacterium fortuitum, Mycobacterium gilvum, Mycobacterium neoaurum, Mycobacterium Phlei, Mycobacterium avium*, or *Mycobacterium vanbaalenii*.

4. A method of preparing steroidal compounds comprising: inoculating the genetically-engineered *Mycobacterium* strain of claim 1 into a culture medium, and adding sterol as a substrate.

5. The method according to claim 4, characterized in that the steroidal compound is sitolactone.

* * * * *

SEQUENCE LISTING

```
<160> NUMBER OF SEQ ID NOS: 16

<210> SEQ ID NO 1
<211> LENGTH: 2659
<212> TYPE: DNA
<213> ORGANISM: Mycobacterium neoaurum
<220> FEATURE:
<221> NAME/KEY: gene
<222> LOCATION: (748)..(1896)
<223> OTHER INFORMATION: Acyl-COA dehydrogenase gene (fadE30)

<400> SEQUENCE: 1
agaacgggtt gatgcacaga tagcggtcgg tgctgctgac ctggccgcac gccgcccagg      60
cggccgaggc gtccagcgac tgccggtgcg cgcaccgcac gcccttgctg cggccggtgg     120
tgccggaggt gaacaggatg tcggacacgt cgtcggggga gaccgcggcg acgcggacgt     180
cgaccgccgc cagcgcatcg gccttgtcgc cgcgggccat gaactcgtcc caggtgccgt     240
cctgcgcgtc gatggggatc cgcacgatat cgcgcagcgc gggcagcgcg gcacggtcga     300
gctgtccggt gcggtctgcg ccgaggaact ccccggcggc gatcaacagt ggagtgcctg     360
tgcgggcaag gatgtcggcc gcctcggagg cggtgtaacg ggtgttcagt gggaccacga     420
tggcgcccgc atagtgggtg gccagcgcgg cgaccaccca atgccaggtg ttcggcgacc     480
```

```
agatggccac gcggtcgccg gcggccactc cgagatcgat cattgccgcg gccgcccgcc    540
ggacctcgtc gcggagctgc cggtaggtga cgtcggtc ggccgtcacc accgcgtcgt    600
ggtcggaaaa ctgcacggca atccggtcca ggaccgccgg aacggttctg attccccggt    660
cgccgtgctc ctgcccaccg gcctgcgggt cgctcgtcat tgacgctcct ctaacaaagc    720
aagtgcttgg taggttagcc tacaagggtg attgaggtcg aggagttccg ggccgaggtc    780
cggcagtggc tcgccgacaa cctcgtcggc gaatatgcag cgctcaaggg cctcggcggc    840
ccgggtcgtg agcatgaggc cttcgaggaa cgccgggcgt ggaatcagca tctggccgcg    900
gcaggcctga cctgcctggg ctggcccgag gagcacggtg gccgcggtct gaccgtcgcg    960
catcgggtgg ccttctatga ggagtacgcc aaggccgacg caccggacaa ggtgaatcac   1020
ctcggtgagg aactgctcgg cccgacgctg atcgcctatg cactcccga acagcagcag   1080
cgtttcctgc cggcatccg ggatgtcacc gagctgtgga gccaggggta ctccgagccc   1140
aatgccggta gcgacctggc caatgtgtcg accactgctg tgctcgacgt tgaccactgg   1200
gtgctcaacg gacagaaagt ctggacatcg ctggcgcact gggcgcagtg gtgcttcgtg   1260
gtcgcgcgat ccgagaaggg gtccaagcga catgccgggc tgtctttcct gctggtgccg   1320
ctggatcagc cgggcgtgca atccgcccg atcatccagc tgaccggcga ctccgagttc   1380
aacgaggtgt tcttcgacga cgcccgcacc gaggccgccc tggtcgtcgg ggaacccggc   1440
gacggctggc gggtcgcgat gggcctgctg accttcgagc gtggtgtgtc cacgctgggc   1500
cagcagatcc gttatgcccg tgagcattcc aacttggtag acctcgccaa gcgcaccggc   1560
gccgccgatg acccactgat ccgcgagcga ctgacccgat cctggaccgg cctgaaggcg   1620
atgcgttcct attcgcttgc gacgatggac gccgaacaac ctggtcaaga caatgtgtcg   1680
aagttgttgt gggccaactg gcatcgcgag ctcggcgaga ttgcgatgga cgtgcagggg   1740
accgctggac tcaccctcga caatggcgaa ttcgacgaat ggcagcggct gtacctgttc   1800
tcccgctccg acaccatcta cggcggatcc aacgagatcc agcgcaacat catcgccgag   1860
cgggtgctcg gcctaccacg agaggccaaa ggctgatgag cctgtcagaa gtacccgaag   1920
agattgccgg acacggactt ctgcagggaa aggtcgtcct ggtcaccgcg gcggccggta   1980
ccgggatcgg gtcgaccacc gcccggcggg ccctgttgga gggcgccgac gtcgtggtct   2040
ccgatttcca cgagcgtcgg ctcggtgaaa cccgagagga gctggcggcg ctgggactgg   2100
gcaaggtcga cgcggtggtt tgcgatgtca cctccaccgc tgccgtggac aacctgatca   2160
ccgaatcggt gcagaaggcg ggccgcctgg acgttctggt caacaatgcc gggctcggtg   2220
ggcagacccc cgtcatcgac atgaccgacg acgaatggga ccgcgtcgtc aacgtgacgc   2280
tgacctcggt catgcgggcg acccgggccg cgttgcgcta cttccgggac gccccgcacg   2340
gcggggtcat cgtcaacaac gccagcgtgc tcggctggcg tgcccagcac tcgcagtcgc   2400
attacgccgc ggccaaggcc ggcgtcatgg cgctgacccg ctgcagcgca atcgaagccg   2460
tcgagtacgg ggtccggatc aatgcggtgt ccccgagcat cgcgcggcac aagttcctgg   2520
aaaagacgtc gtctgcagag ctgctggacc gtctcgccgg cgacgaggcc ttcggccgcg   2580
cggcggagcc ctgggagatc gcgtccacca tcgccttttt ggccagcgat tactccagtt   2640
atctgaccgg agaggtcat                                                2659
```

<210> SEQ ID NO 2
<211> LENGTH: 382
<212> TYPE: PRT

<213> ORGANISM: Mycobacterium neoaurum

<400> SEQUENCE: 2

```
Val Ile Glu Val Glu Phe Arg Ala Glu Val Arg Gln Trp Leu Ala
1               5                   10                  15

Asp Asn Leu Val Gly Glu Tyr Ala Ala Leu Lys Gly Leu Gly Gly Pro
            20                  25                  30

Gly Arg Glu His Glu Ala Phe Glu Glu Arg Arg Ala Trp Asn Gln His
                35                  40                  45

Leu Ala Ala Ala Gly Leu Thr Cys Leu Gly Trp Pro Glu Glu His Gly
    50                  55                  60

Gly Arg Gly Leu Thr Val Ala His Arg Val Ala Phe Tyr Glu Glu Tyr
65                  70                  75                  80

Ala Lys Ala Asp Ala Pro Asp Lys Val Asn His Leu Gly Glu Glu Leu
                85                  90                  95

Leu Gly Pro Thr Leu Ile Ala Tyr Gly Thr Pro Glu Gln Gln Gln Arg
            100                 105                 110

Phe Leu Pro Gly Ile Arg Asp Val Thr Glu Leu Trp Ser Gln Gly Tyr
        115                 120                 125

Ser Glu Pro Asn Ala Gly Ser Asp Leu Ala Asn Val Ser Thr Thr Ala
    130                 135                 140

Val Leu Asp Val Asp His Trp Val Leu Asn Gly Gln Lys Val Trp Thr
145                 150                 155                 160

Ser Leu Ala His Trp Ala Gln Trp Cys Phe Val Val Ala Arg Ser Glu
                165                 170                 175

Lys Gly Ser Lys Arg His Ala Gly Leu Ser Phe Leu Leu Val Pro Leu
            180                 185                 190

Asp Gln Pro Gly Val Gln Ile Arg Pro Ile Ile Gln Leu Thr Gly Asp
        195                 200                 205

Ser Glu Phe Asn Glu Val Phe Phe Asp Asp Ala Arg Thr Glu Ala Ala
    210                 215                 220

Leu Val Val Gly Glu Pro Gly Asp Gly Trp Arg Val Ala Met Gly Leu
225                 230                 235                 240

Leu Thr Phe Glu Arg Gly Val Ser Thr Leu Gly Gln Gln Ile Arg Tyr
                245                 250                 255

Ala Arg Glu His Ser Asn Leu Val Asp Leu Ala Lys Arg Thr Gly Ala
            260                 265                 270

Ala Asp Asp Pro Leu Ile Arg Glu Arg Leu Thr Arg Ser Trp Thr Gly
        275                 280                 285

Leu Lys Ala Met Arg Ser Tyr Ser Leu Ala Thr Met Asp Ala Glu Gln
    290                 295                 300

Pro Gly Gln Asp Asn Val Ser Lys Leu Leu Trp Ala Asn Trp His Arg
305                 310                 315                 320

Glu Leu Gly Glu Ile Ala Met Asp Val Gln Gly Thr Ala Gly Leu Thr
                325                 330                 335

Leu Asp Asn Gly Glu Phe Asp Glu Trp Gln Arg Leu Tyr Leu Phe Ser
            340                 345                 350

Arg Ser Asp Thr Ile Tyr Gly Gly Ser Asn Glu Ile Gln Arg Asn Ile
        355                 360                 365

Ile Ala Glu Arg Val Leu Gly Leu Pro Arg Glu Ala Lys Gly
    370                 375                 380
```

<210> SEQ ID NO 3
<211> LENGTH: 2926

```
<212> TYPE: DNA
<213> ORGANISM: Mycobacterium neoaurum
<220> FEATURE:
<221> NAME/KEY: gene
<222> LOCATION: (889)..(2037)
<223> OTHER INFORMATION: Acyl-CoA dehydrogenase gene (fadE31)

<400> SEQUENCE: 3
tcaacccgtt ctttcacaac ttcggttaca aggcaggcat tctcgcgtgc ttgcaaaccg      60
gagccacgct ctatcccctg ctcaccttcg atcccgagca ggccatgaag gccgtcgccg     120
agcaccggat caccgtgctg ccgggtccgc ccacgatcta ccagaccctg ctggaccacc     180
cacgccgtgc ggactatgac ctgtcgtcgc tgcggttcgc ggtgaccggg gccgccgtcg     240
tgcccgtggt gctgatcgaa cggatgcaat ccgagctcga catcgagatc gtgttgaccg     300
cctacggatt gaccgaggcg gccggcttcg gcaccatgtg ccgagccgat gacgatgccg     360
tcaccgtggc caccacctgc gggcgcccca tcgccgactt cgatcttcgc atcgacgagt     420
ccggcgaggt tctactgcgc gggccgaacg tcatgctcgg ctacctcgat gatccggagg     480
ccaccgcggc cgccatcgac gacgagggtt ggttgcacac cggcgatatc gggaagctcg     540
acgacgcagg caatctcacc atcaccgacc gactcaagga catgtacatc tgcggtgggt     600
tcaatgtcta ccccgccgag atcgaacagg tactggcgcg tctcgagggg gtggccgagt     660
ccgcggtgat cggcgtcccc gacgaacgcc tcggcgaggt cggcagggcc ttcgtggtgg     720
ccaagcccgg tgccggtctc gacgaggaga ccgtcatcgc ccacacccgt acacatctgg     780
cgaatttcaa ggtgccccgt tcggtggtgt tcctcgacgt gctgccacgc aaccctggag     840
gcaaagtggt caaaccgatg ctgcgtgaac tcgacgggag gagctgagat ggacctgaca     900
ttcgacgagg acagcgaggc tttccgccac gaggtccgcg aattcctcga cgccaaccgt     960
gatcacttcc ccaccaagtc ctatgacacc cgtgagggat tcgaccagca tcggacctgg    1020
gacaaggtgc tcttcgacgc cgggttgtcg gtgatcgcct ggccgcagaa gtacggcggc    1080
cgggatgcca gcctgctgca atgggtggtg ttcgaggagg agtacttccg cgccggtgcc    1140
cccggccgag ccagcgccaa cggcacctcg atgctggcgc cgacgctctt cgcgcacggt    1200
acagaagaac agctggaccg ggtgctgccc aaaatggcca gcggcgagga gatctgggcg    1260
caggcgtggt ccgagcccga gtcgggtagt gacctggcat cgctgcgctc caccgccacc    1320
cgcaccgacg gcggctggct gctcaacggt cagaagatat ggagttcgcg cgccgtgttc    1380
ggcgaacggg cattcggcct cttccggtcc gacccgcagg cgcagcgaca aagggcctg    1440
acgtacttca tgttcgacct gcatgcccag ggtgtcacgg tccgcccgat cgcccagctc    1500
ggtggtgata ccggtttcgg tgagatcttc ctcgacgatg tgttcgtccc gacgaggac    1560
gtcatcggcg aggcgaatga cggctggcgc gggcgatga gcacgtcgag caatgaacgc    1620
ggcatgtccc tgcgcagccc cgcgcgattc ctggcaccgg cggaacgact tgtgcagcaa    1680
tggaagaaca atcccgatcc ggttttcacc gatcgcgttg ccgatgcctg gatcaaggct    1740
caggcctatc gactgcacac cttcggcacc gtcacccggc tggccggtgg tggtgaactc    1800
ggcgcggaat cctcggtcac gaaggtcttc tggtcggatc tggatgtcgc actgcaccag    1860
accgcactgg atctgcaggg cgccgacgcc gagatcgtcg accacacgac cgagggtctg    1920
ctgttcgcgc tcggcggccc gatctatgcc ggcaccaacg agatccagcg caacataatc    1980
gccgagcggc tgctggggct gccacgtgag atttctgggg ggaaacccaa gtcatgaact    2040
tcgagataga cgaccagcag cgtgatttcg cgtcgagcat cgatgccgca ctcggcgcgg    2100
```

-continued

```
ccgatgtccc gtccgccatc cgggcctggg ccgacggtga ctctgccccc gcccgcaagg    2160
tatgggcaca gctcaccgac ctcggcgtga ccgccctctc ggtggccgag aagttcgacg    2220
ggatcgaggc tcaaccgatc gatctggtgg tggcattgga acggctgggt tactgggccg    2280
tcccgggtcc ggtcaccgaa tctgttgccg tggcacccat cctgctcgcc gatgacgagc    2340
ggtccgcggc actggctgcc ggggagctga tcgccaccgt ggcacttccg ccacaggtgc    2400
cctatgccgt caacgccgac ttcgcggggt tgacgctgtt ggccggagat ggccgggtgg    2460
ccgaggcgac accgggttcc gcgcacgatt cggtcgatcc cacgcgacgc ctcttcgagg    2520
tcgacgcatc cggggacgga cagtccgccg ataccgcacg cgcctacgag ttcggggtgt    2580
tggccacggc cgcccagctg gtcggggcgg acaggcgat gctggacctg tcggtggcct    2640
atgccaagca gcgcacccaa ttcgccgggt gatcggctc ctatcaggcg atcaagcaca    2700
agctcgccga tgtgcacatc gcggtcgaga tggcgcgccc gctggtccac ggggcggcgt    2760
tggcgcttgc cgacggctca ccggacactc cccgcgatgt gagcgcggcc aaggtggccg    2820
ccgccgatgc cgcgctgttg gcagcgcgtt cgtcactgca gacccacggc gccatcggat    2880
tcacccagga acacgacctg tcgctgttgc tccttcgagt gcaggc                   2926
```

<210> SEQ ID NO 4
<211> LENGTH: 382
<212> TYPE: PRT
<213> ORGANISM: Mycobacterium neoaurum

<400> SEQUENCE: 4

```
Met Asp Leu Thr Phe Asp Glu Asp Ser Glu Ala Phe Arg His Glu Val
1               5                   10                  15

Arg Glu Phe Leu Asp Ala Asn Arg Asp His Phe Pro Thr Lys Ser Tyr
            20                  25                  30

Asp Thr Arg Glu Gly Phe Asp Gln His Arg Thr Trp Asp Lys Val Leu
        35                  40                  45

Phe Asp Ala Gly Leu Ser Val Ile Ala Trp Pro Gln Lys Tyr Gly Gly
    50                  55                  60

Arg Asp Ala Ser Leu Leu Gln Trp Val Val Phe Glu Glu Tyr Phe
65                  70                  75                  80

Arg Ala Gly Ala Pro Gly Arg Ala Ser Ala Asn Gly Thr Ser Met Leu
                85                  90                  95

Ala Pro Thr Leu Phe Ala His Gly Thr Glu Glu Leu Asp Arg Val
            100                 105                 110

Leu Pro Lys Met Ala Ser Gly Glu Glu Ile Trp Ala Gln Ala Trp Ser
        115                 120                 125

Glu Pro Glu Ser Gly Ser Asp Leu Ala Ser Leu Arg Ser Thr Ala Thr
    130                 135                 140

Arg Thr Asp Gly Gly Trp Leu Leu Asn Gly Gln Lys Ile Trp Ser Ser
145                 150                 155                 160

Arg Ala Val Phe Gly Glu Arg Ala Phe Gly Leu Phe Arg Ser Asp Pro
                165                 170                 175

Gln Ala Gln Arg His Lys Gly Leu Thr Tyr Phe Met Phe Asp Leu His
            180                 185                 190

Ala Gln Gly Val Thr Val Arg Pro Ile Ala Gln Leu Gly Gly Asp Thr
        195                 200                 205

Gly Phe Gly Glu Ile Phe Leu Asp Asp Val Phe Val Pro Asp Glu Asp
    210                 215                 220

Val Ile Gly Glu Ala Asn Asp Gly Trp Arg Ala Ala Met Ser Thr Ser
```

```
                    225                 230                 235                 240
        Ser Asn Glu Arg Gly Met Ser Leu Arg Ser Pro Ala Arg Phe Leu Ala
                        245                 250                 255

Pro Ala Glu Arg Leu Val Gln Gln Trp Lys Asn Asn Pro Asp Pro Val
                    260                 265                 270

Phe Thr Asp Arg Val Ala Asp Ala Trp Ile Lys Ala Gln Ala Tyr Arg
                275                 280                 285

Leu His Thr Phe Gly Thr Val Thr Arg Leu Ala Gly Gly Gly Glu Leu
            290                 295                 300

Gly Ala Glu Ser Ser Val Thr Lys Val Phe Trp Ser Asp Leu Asp Val
        305                 310                 315                 320

Ala Leu His Gln Thr Ala Leu Asp Leu Gln Gly Ala Asp Ala Glu Ile
                        325                 330                 335

Val Asp His Thr Thr Glu Gly Leu Leu Phe Ala Leu Gly Gly Pro Ile
                    340                 345                 350

Tyr Ala Gly Thr Asn Glu Ile Gln Arg Asn Ile Ile Ala Glu Arg Leu
                355                 360                 365

Leu Gly Leu Pro Arg Glu Ile Ser Gly Gly Lys Pro Lys Ser
            370                 375                 380

<210> SEQ ID NO 5
<211> LENGTH: 2731
<212> TYPE: DNA
<213> ORGANISM: Mycobacterium neoaurum
<220> FEATURE:
<221> NAME/KEY: gene
<222> LOCATION: (889)..(1845)
<223> OTHER INFORMATION: Acyl-CoA dehydrogenase gene (fadE32)

<400> SEQUENCE: 5
ccgagccagc gccaacggca cctcgatgct ggcgccgacg ctcttcgcgc acggtacaga      60
agaacagctg gaccgggtgc tgcccaaaat ggccagcggc gaggagatct gggcgcaggc     120
gtggtccgag cccgagtcgg gtagtgacct ggcatcgctg cgctccaccg ccacccgcac     180
cgacggcggc tggctgctca acggtcagaa gatatggagt tcgcgcgccg tgttcggcga     240
acgggcattc ggcctcttcc ggtccgaccc gcaggcgcag cgacacaagg gcctgacgta     300
cttcatgttc gacctgcatg cccagggtgt cacggtccgc ccgatcgccc agctcggtgg     360
tgataccggt ttcggtgaga tcttcctcga cgatgtgttc gtccccgacg aggacgtcat     420
cggcgaggcg aatgacggct ggcgcgcggc gatgagcacg tcgagcaatg aacgcggcat     480
gtccctgcgc agccccgcgc gattcctggc accggcggaa cgacttgtgc agcaatggaa     540
gaacaatccc gatccggttt tcaccgatcg cgttgccgat gcctggatca aggctcaggc     600
ctatcgactg cacaccttcg gcaccgtcac ccggctggcc ggtggtggtg aactcggcgc     660
ggaatcctcg gtcacgaagg tcttctggtc ggatctggat gtcgcactgc accagaccgc     720
actggatctg cagggcgccg acgccgagat cgtcgaccac acgaccgagg tctgctgtt      780 cgcgctcggc ggcccgatct atgccggcac caacgagatc cagcgcaaca taatcgccga     840
gcggctgctg gggctgccac gtgagatttc tgggggaaa cccaagtcat gaacttcgag     900
atagacgacc agcagcgtga tttcgcgtcg agcatcgatg ccgcactcgg cgcggccgat     960
gtcccgtccg ccatccgggc ctgggccgac ggtgactctg ccccgcccg caaggtatgg    1020 gcacagctca ccgacctcgg cgtgaccgcc ctctcggtgg ccgagaagtt cgacgggatc    1080
gaggctcaac cgatcgatct ggtggtggca ttggaacggc tgggttactg ggccgtcccg    1140
```

```
ggtccggtca ccgaatctgt tgccgtggca cccatcctgc tcgccgatga cgagcggtcc    1200
gcggcactgg ctgccgggga gctgatcgcc accgtggcac ttccgccaca ggtgccctat    1260
gccgtcaacg ccgacttcgc ggggttgacg ctgttggccg agatggccg  ggtggccgag    1320 gcgacaccgg gttccgcgca cgattcggtc gatcccacgc gacgcctctt cgaggtcgac    1380
gcatccgggg acggacagtc cgccgatacc gcacgcgcct acgagttcgg ggtgttggcc    1440
acggccgccc agctggtcgg ggcgggacag gcgatgctgg acctgtcggt ggcctatgcc    1500
aagcagcgca cccaattcgg ccgggtgatc ggctcctatc aggcgatcaa gcacaagctc    1560
gccgatgtgc acatcgcggt cgagatggcg cgcccgctgg tccacggggc ggcgttggcg    1620
cttgccgacg gctcaccgga cactgcccgc gatgtgagcg cggccaaggt ggccgccgcc    1680
gatgccgcgt tgttggcagc gcgttcgtca ctgcagaccc acggcgccat cggattcacc    1740
caggaacacg acctgtcgct gttgctcctt cgagtgcagg cattgcgctc ggcctggggt    1800 gaccccgaccc tgcaccgtcg ccgcctgttg gaggtccttt cgtgagtgaa gaacgcgaac    1860
tgctgcgctc cactgttgcg gcactggtcg acaagcacgc cacccccgag gcggtccgta    1920
ccgcgatgga gtccgaccgc ggctacgacg agtcgctgtg gaagctgttg tgcgagcagg    1980
tcggtgccgg ggcgctggtc atccccgatg acctcggtgg ggccggtggt gagctcgccg    2040
acgccgccgt cgtcttggag gagctcggta aggcgctggt acccacgccg ctgctcggca    2100
ccacactggc cgagctggcg ctactgcatg ccggggacca cgagtcgttg gaagggttgg    2160
ccgagggcgc ctcgatcggc acggtggtct tcgatcccga gtatgtcgtc aacggtgaca    2220
tcgccgatat cgtgatcgcc gccgacggga ccgagctgac caggtggacg aatgtcaccg    2280
cgcagccgca cgcgacgatg gacctgaccc gacgactgtc gtcggtgacc gcgggcgaga    2340
ccgccgcgct gggaaccgat cccggccttt ccgacaccgc tgccctgttg ctggccgccg    2400
aacagatcgg tgccgccgcc cgagcgctcg acctcacggt ggcctacaca aaggaccggg    2460
tgcagttcgg caggccgatc ggcagcttcc aggcactcaa gcaccggatg ccgatctct     2520 acgtcacggt gcaatcggcg cgggcggtca tctacgacgc catcgccgat ccgtccccag    2580
cgtcggcctc gctggcacgg tgttcgcca  gcgaagccct gaccgacgtg gccgccgaag    2640
cggtgcagct ccacggcggc attgccatca cctgggagca cgacatccag ctgtacttca    2700
agcgggcgca tgccagcgcc cagctgctcg g                                    2731
```

<210> SEQ ID NO 6
<211> LENGTH: 318
<212> TYPE: PRT
<213> ORGANISM: Mycobacterium neoaurum

<400> SEQUENCE: 6

```
Met Asn Phe Glu Ile Asp Asp Gln Gln Arg Asp Phe Ala Ser Ser Ile
1               5                   10                  15

Asp Ala Ala Leu Gly Ala Ala Asp Val Pro Ser Ala Ile Arg Ala Trp
            20                  25                  30

Ala Asp Gly Asp Ser Ala Pro Ala Arg Lys Val Trp Ala Gln Leu Thr
        35                  40                  45

Asp Leu Gly Val Thr Ala Leu Ser Val Ala Glu Lys Phe Asp Gly Ile
    50                  55                  60

Glu Ala Gln Pro Ile Asp Leu Val Val Ala Leu Glu Arg Leu Gly Tyr
65                  70                  75                  80

Trp Ala Val Pro Gly Pro Val Thr Glu Ser Val Ala Val Ala Pro Ile
                85                  90                  95
```

Leu Leu Ala Asp Asp Glu Arg Ser Ala Ala Leu Ala Ala Gly Glu Leu
            100                 105                 110

Ile Ala Thr Val Ala Leu Pro Pro Gln Val Pro Tyr Ala Val Asn Ala
        115                 120                 125

Asp Phe Ala Gly Leu Thr Leu Leu Ala Gly Asp Gly Arg Val Ala Glu
130                 135                 140

Ala Thr Pro Gly Ser Ala His Asp Ser Val Asp Pro Thr Arg Arg Leu
145                 150                 155                 160

Phe Glu Val Asp Ala Ser Gly Asp Gly Gln Ser Ala Asp Thr Ala Arg
                165                 170                 175

Ala Tyr Glu Phe Gly Val Leu Ala Thr Ala Gln Leu Val Gly Ala
            180                 185                 190

Gly Gln Ala Met Leu Asp Leu Ser Val Ala Tyr Ala Lys Gln Arg Thr
        195                 200                 205

Gln Phe Gly Arg Val Ile Gly Ser Tyr Gln Ala Ile Lys His Lys Leu
    210                 215                 220

Ala Asp Val His Ile Ala Val Glu Met Ala Arg Pro Leu Val His Gly
225                 230                 235                 240

Ala Ala Leu Ala Leu Ala Asp Gly Ser Pro Asp Thr Ala Arg Asp Val
                245                 250                 255

Ser Ala Ala Lys Val Ala Ala Asp Ala Ala Leu Leu Ala Ala Arg
            260                 265                 270

Ser Ser Leu Gln Thr His Gly Ala Ile Gly Phe Thr Gln Glu His Asp
        275                 280                 285

Leu Ser Leu Leu Leu Arg Val Gln Ala Leu Arg Ser Ala Trp Gly
    290                 295                 300

Asp Pro Thr Leu His Arg Arg Leu Leu Glu Val Leu Ser
305                 310                 315

<210> SEQ ID NO 7
<211> LENGTH: 2701
<212> TYPE: DNA
<213> ORGANISM: Mycobacterium neoaurum
<220> FEATURE:
<221> NAME/KEY: gene
<222> LOCATION: (886)..(1821)
<223> OTHER INFORMATION: Acyl-CoA dehydrogenase gene (fadE33)

<400> SEQUENCE: 7

```
cgatgtcccg tccgccatcc gggcctgggc cgacggtgac tctgccccg cccgcaaggt      60
atgggcacag ctcaccgacc tcggcgtgac cgccctctcg gtggccgaga agttcgacgg    120
gatcgaggct caaccgatcg atctggtggt ggcattggaa cggctgggtt actgggccgt    180
cccgggtccg gtcaccgaat ctgttgccgt ggcacccatc ctgctcgccg atgacgagcg    240
gtccgcggca ctggctgccg gggagctgat cgccaccgtg gcacttccgc acaggtgcc    300
ctatgccgtc aacgccgact cgcgggggtt gacgctgttg gccggagatg gccggtggc    360
cgaggcgaca ccgggttccg cgcacgattc ggtcgatccc acgcgacgcc tcttcgaggt    420
cgacgcatcc ggggacggac agtccgccga taccgcacgc gcctacgagt tcggggtgtt    480
ggccacggcc gcccagctgg tcgggcggg acaggcgatg ctggacctgt cggtggccta    540
tgccaagcag cgcacccaat tcggccgggt gatcggctcc tatcaggcga tcaagcacaa    600
gctcgccgat gtgcacatcg cggtcgagat ggcgcgcccg ctggtccacg ggcggcgtt    660
ggcgcttgcc gacggctcac cggacactgc ccgcgatgtg agcgcggcca aggtggccgc    720
```

```
cgccgatgcc gcgctgttgg cagcgcgttc gtcactgcag acccacggcg ccatcggatt    780
cacccaggaa cacgacctgt cgctgttgct ccttcgagtg caggcattgc gctcggcctg    840
gggtgacccg accctgcacc gtcgccgcct gttggaggtc ctttcgtgag tgaagaacgc    900
gaactgctgc gctccactgt tgcggcactg gtcgacaagc acgccacccc cgaggcggtc    960
cgtaccgcga tggagtccga ccgcggctac gacgagtcgc tgtggaagct gttgtgcgag   1020
caggtcggtg ccgcggcgct ggtcatcccc gatgacctcg gtgggccgg tggtgagctc    1080 gccgacgccg ccgtcgtctt ggaggagctc ggtaaggcgc tggtacccac gccgctgctc    1140
ggcaccacac tggccgagct ggcgctactg catgccgggg accacgagtc gttggaaggg    1200
ttggccgagg gcgcctcgat cggcacggtg gtcttcgatc ccgagtatgt cgtcaacggt    1260
gacatcgccg atatcgtgat cgccgccgac gggaccgagc tgaccaggtg gacgaatgtc    1320
accgcgcagc cgcacgcgac gatggacctg acccgacgac tgtcgtcggt gaccgcgggc    1380
gagaccgccg cgctgggaac cgatcccggc ctttccgaca ccgctgccct gttgctggcc    1440
gccgaacaga tcggtgccgc cgcccgagcg ctcgacctca cggtggccta cacaaaggac    1500
cgggtgcagt tcggcaggcc gatcggcagc ttccaggcac tcaagcaccg gatggccgat    1560
ctctacgtca cggtgcaatc ggcgcggggcg gtcatctacg acgccatcgc cgatccgtcc    1620
```

-continued

```
Asp Lys His Ala Thr Pro Glu Ala Val Arg Thr Ala Met Glu Ser Asp
         20                  25                  30

Arg Gly Tyr Asp Glu Ser Leu Trp Lys Leu Leu Cys Glu Gln Val Gly
     35                  40                  45

Ala Ala Ala Leu Val Ile Pro Asp Asp Leu Gly Gly Ala Gly Gly Glu
 50                  55                  60

Leu Ala Asp Ala Ala Val Val Leu Glu Glu Leu Gly Lys Ala Leu Val
65                  70                  75                  80

Pro Thr Pro Leu Leu Gly Thr Thr Leu Ala Glu Leu Ala Leu Leu His
             85                  90                  95

Ala Gly Asp His Glu Ser Leu Glu Gly Leu Ala Glu Gly Ala Ser Ile
        100                 105                 110

Gly Thr Val Val Phe Asp Pro Glu Tyr Val Val Asn Gly Asp Ile Ala
    115                 120                 125

Asp Ile Val Ile Ala Ala Asp Gly Thr Glu Leu Thr Arg Trp Thr Asn
130                 135                 140

Val Thr Ala Gln Pro His Ala Thr Met Asp Leu Thr Arg Arg Leu Ser
145                 150                 155                 160

Ser Val Thr Ala Gly Glu Thr Ala Ala Leu Gly Thr Asp Pro Gly Leu
                165                 170                 175

Ser Asp Thr Ala Ala Leu Leu Leu Ala Ala Glu Gln Ile Gly Ala Ala
            180                 185                 190

Ala Arg Ala Leu Asp Leu Thr Val Ala Tyr Thr Lys Asp Arg Val Gln
        195                 200                 205

Phe Gly Arg Pro Ile Gly Ser Phe Gln Ala Leu Lys His Arg Met Ala
    210                 215                 220

Asp Leu Tyr Val Thr Val Gln Ser Ala Arg Ala Val Ile Tyr Asp Ala
225                 230                 235                 240

Ile Ala Asp Pro Ser Pro Ala Ser Ala Ser Leu Ala Arg Val Phe Ala
                245                 250                 255

Ser Glu Ala Leu Thr Asp Val Ala Glu Ala Val Gln Leu His Gly
            260                 265                 270

Gly Ile Ala Ile Thr Trp Glu His Asp Ile Gln Leu Tyr Phe Lys Arg
        275                 280                 285

Ala His Ala Ser Ala Gln Leu Leu Gly Pro Pro Arg Glu His Leu Arg
    290                 295                 300

Arg Leu Glu Ala Glu Val Phe
305                 310

<210> SEQ ID NO 9
<211> LENGTH: 34
<212> TYPE: DNA
<213> ORGANISM: Artificial Sequence
<220> FEATURE:
<223> OTHER INFORMATION: Dalian Takara Corporation

<400> SEQUENCE: 9
gcgcaagctt ggtcagataa ctggagtagt cgct                              34

<210> SEQ ID NO 10
<211> LENGTH: 34
<212> TYPE: DNA
<213> ORGANISM: Artificial Sequence
<220> FEATURE:
<223> OTHER INFORMATION: Dalian Takara Corporation

<400> SEQUENCE: 10
```
tataccatgg aagctgttgt gggccaactg gcat    34

<210> SEQ ID NO 11
<211> LENGTH: 35
<212> TYPE: DNA
<213> ORGANISM: Artificial Sequence
<220> FEATURE:
<223> OTHER INFORMATION: Dalian Takara Corporation

<400> SEQUENCE: 11
tataccatgg ctcatagaag gccacccggt gcgcg    35

<210> SEQ ID NO 12
<211> LENGTH: 34
<212> TYPE: DNA
<213> ORGANISM: Artificial Sequence
<220> FEATURE:
<223> OTHER INFORMATION: Dalian Takara Corporation

<400> SEQUENCE: 12
tataggtacc gggttgatgc acaggtagcg gtcg    34

<210> SEQ ID NO 13
<211> LENGTH: 35
<212> TYPE: DNA
<213> ORGANISM: Artificial Sequence
<220> FEATURE:
<223> OTHER INFORMATION: Dalian Takara Corporation

<400> SEQUENCE: 13
gcgcaagctt tcaacccgtt ctttcacaac ttcgg    35

<210> SEQ ID NO 14
<211> LENGTH: 35
<212> TYPE: DNA
<213> ORGANISM: Artificial Sequence
<220> FEATURE:
<223> OTHER INFORMATION: Dalian Takara Corporation

<400> SEQUENCE: 14
tataggatcc gcgtcgaaga gcaccttgtc ccagg    35

<210> SEQ ID NO 15
<211> LENGTH: 35
<212> TYPE: DNA
<213> ORGANISM: Artificial Sequence
<220> FEATURE:
<223> OTHER INFORMATION: Dalian Takara Corporation

<400> SEQUENCE: 15
tataggatcc tggcacgggt gttcgccagc gaagc    35

<210> SEQ ID NO 16
<211> LENGTH: 35
<212> TYPE: DNA
<213> ORGANISM: Artificial Sequence
<220> FEATURE:
<223> OTHER INFORMATION: Dalian Takara Corporation

<400> SEQUENCE: 16
tataggtacc ggtgatgacc acggcgtcca tgtcg    35